US007094573B2

(12) United States Patent
Laird

(10) Patent No.: US 7,094,573 B2

(45) Date of Patent: Aug. 22, 2006

(54) MODIFIED SHINE-DALGARNO SEQUENCES AND METHODS OF USE THEREOF

(75) Inventor: Michael W. Laird, Germantown, MD (US)

(73) Assignee: Human Genome Sciences, Inc., Rockville, MD (US)

(*) Notice: Subject to any disclaimer, the term of this patent is extended or adjusted under 35 U.S.C. 154(b) by 0 days.

(21) Appl. No.: 11/004,853

(22) Filed: Dec. 7, 2004

(65) Prior Publication Data

US 2005/0153339 A1 Jul. 14, 2005

Related U.S. Application Data

(63) Continuation of application No. PCT/US03/19786, filed on Jun. 25, 2003.

(60) Provisional application No. 60/406,630, filed on Aug. 29, 2002, provisional application No. 60/391,433, filed on Jun. 26, 2002.

(51) Int. Cl.

| | |
|---|---|
| ***C12P 21/00*** | (2006.01) |
| ***C07H 21/04*** | (2006.01) |
| ***C12N 15/63*** | (2006.01) |
| ***C12N 1/21*** | (2006.01) |
| ***C12N 15/66*** | (2006.01) |

(52) U.S. Cl. ............... 435/69.1; 435/320.1; 435/252.3; 435/476; 536/24.1

(58) Field of Classification Search ..................... None
See application file for complete search history.

(56) References Cited

U.S. PATENT DOCUMENTS

| | | | |
|---|---|---|---|
| 3,979,506 | A | 9/1976 | Smith |
| 4,358,595 | A | 11/1982 | Ghosh et al. |
| 4,582,789 | A | 4/1986 | Sheldon, III et al. |
| 5,109,124 | A | 4/1992 | Ramachandran et al. |
| 5,317,098 | A | 5/1994 | Shizuya et al. |
| 5,663,319 | A | 9/1997 | Bittner et al. |
| 6,096,545 | A | 8/2000 | LeFebvre et al. |
| 6,194,168 | B1 | 2/2001 | Gentz et al. |
| 2002/0039588 | A1 | 4/2002 | Collier et al. |
| 2002/0048590 | A1 | 4/2002 | Klimpel et al. |
| 2002/0051791 | A1 | 5/2002 | Galloway et al. |

FOREIGN PATENT DOCUMENTS

| | | |
|---|---|---|
| WO | WO-99/16858 | 4/1999 |
| WO | WO00/56883 | 9/2000 |
| WO | WO01/82788 | 11/2001 |

OTHER PUBLICATIONS

Pearce, GenEmbl database, Accesssion No. AL160036, Sep. 30, 2000.*

Zhao et al., EST Database, Accession No. AZ102942, May 9, 2000.*

Chauhan, V. et al., "Constitutive expression of protective antigen gene of *Bacillus anthracis* in *Escherichia coli," Biochem. Biophys. Res. Commun.* 283(2):308-315 (2001).

Gupta, P. et al., "Expression and purification of the recombinant protective antigen of *Bacillus anthracis," Protein Expr. Purif.* 7:33-38 (1996).

Komarova et al., "Extensive complementarity of the Shine-Dalgarno region and 3'-terminal sequence of 16S ribosomal RNA is inefficient for translation in vivo," *Bioorg. Khim.* 27(4):282-290 (2001) (in Russian; abstract in English).

Sellman, B.R. et al., "Point mutations in anthrax protective antigen that blocks translocation," *J. Biol. Chem.* 276(11):8371-8376 (2001).

Sharma, M. et al., "Expression and purification of anthrax protective antigen from *Escherichia coli," Protein Expr. Purif.* 16(3):369-376 (1999).

Shine & Dalgarno, "The 3'-Terminal Sequence of *Escherichia coli* 16S Ribosomal RNA: Complementarity to Nonsense Triplets and Ribosome Binding Sites," *Proc. Natl. Acad. Sci. USA* 71(4):1342-1346 (1976).

Stenstrom et al., "Codon bias at the 3'-side of the initiation codon is correlated with translation initiation efficiency in *Escherichia coli," Gene*263(1-2):273-284 (2001).

Stenström et al., "Cooperative effects by the initiation codon and its flanking regions on translation initiation," *Gene* 273(2):259-265 (2001).

Kammerer et al., "Functional dissection of *Escherichia coli* promoters: information in the transcribed region is involved in late steps of the overall process," *EMBO J.* 5(11):2995-3000 (1986).

Supplementary European Search Report, European Application No. EP 03 76 1989, mailed Sep. 16, 2005.

* cited by examiner

*Primary Examiner*—Nancy Vogel
(74) *Attorney, Agent, or Firm*—Human Genome Sciences, Inc.

(57) ABSTRACT

Novel Shine-Dalgarno (ribosome binding site) sequences, vectors containing such sequences, and host cells transformed with these vectors are provided. Methods of use of such sequences, vectors, and host cells for the efficient production of proteins and fragments thereof in prokaryotic systems are also provided. In particular embodiments of the invention, compounds and methods for high efficiency production of soluble protein in prokaryotic systems are provided.

20 Claims, 6 Drawing Sheets

Shine Dalgarno Sequences

SEQ ID NO:2 ATTATAAAGGAAAAATTA
SEQ ID NO:17 ATTAAAGAGGAGAAATTA

FIG. 1 pHE6 Vector Map
No Insert pHE6 Vector Map With wtPA Insert

STII-TL6 in pHE6

STII-TL6 in pHE4

Purified PA
Expressed Using pHE6

SEQUENCE LISTING

<160> NUMBER OF SEQ ID NOS: 18

<210> SEQ ID NO 1
<211> LENGTH: 3979
<212> TYPE: DNA
<213> ORGANISM: Artificial sequence
<220> FEATURE:
<223> OTHER INFORMATION: pHE6 expression plasmid including novel
Shine-Dalgarno sequence
<220> FEATURE:
<221> NAME/KEY: promoter
<222> LOCATION: (27)..(31)
<223> OTHER INFORMATION: -30 region of promoter
<220> FEATURE:
<221> NAME/KEY: promoter
<222> LOCATION: (50)..(55)
<223> OTHER INFORMATION: -12 region of promoter
<220> FEATURE:
<221> NAME/KEY: misc_feature
<222> LOCATION: (32)..(49)
<223> OTHER INFORMATION: First operator sequence
<220> FEATURE:
<221> NAME/KEY: misc_feature
<222> LOCATION: (63)..(81)
<223> OTHER INFORMATION: Second operator sequence
<220> FEATURE:
<221> NAME/KEY: RBS
<222> LOCATION: (92)..(101)
<223> OTHER INFORMATION: Shine-Dalgarno sequence
<220> FEATURE:
<221> NAME/KEY: terminator
<222> LOCATION: (135)..(156)
<223> OTHER INFORMATION: Tsc terminator sequence
<220> FEATURE:
<221> NAME/KEY: rep_origin
<222> LOCATION: (771)..(799)
<223> OTHER INFORMATION: ori C sequence
<220> FEATURE:
<221> NAME/KEY: misc_feature
<222> LOCATION: (1498)..(2457)

-continued

```
<223> OTHER INFORMATION: Lac I repressor gene
<220> FEATURE:
<221> NAME/KEY: misc_feature
<222> LOCATION: (2835)..(3629)
<223> OTHER INFORMATION: Kanamycin resistance gene (reverse orientation)

<400> SEQUENCE: 1

aagcttaaaa aactgcaaaa aatagtttga cttgtgagcg gataacaatt aagatgtacc     60

caattgtgag cggataacaa tttcacacat tataaaggaa aaattacata tgaaggatcc    120

aaggtacctg agtagggcgt ccgatcgacg gacgcctttt ttttgaattc gtaatcatgt    180

catagctgtt tcctgtgtga aattgttatc cgctcacaat tccacacaac atacgagccg    240

gaagcataaa gtgtaaagcc tggggtgcct aatgagtgag ctaactcaca ttaattgcgt    300

tgcgctcact gcccgctttc cagtcgggaa acctgtcgtg ccagctgcat taatgaatcg    360

gccaacgcgc ggggagaggc ggtttgcgta ttgggcgctc ttccgcttcc tcgctcactg    420

actcgctgcg ctcggtcgtt cggctgcggc gagcggtatc agctcactca aaggcggtaa    480

tacggttatc cacagaatca ggggagaacg caggaaagaa catgtgagca aaaggccagc    540

aaaaggccag gaaccgtaaa aaggccgcgt tgctggcgtt tttccatagg ctccgccccc    600

ctgacgagca tcacaaaaat cgacgctcaa gtcagaggtg gcgaaacccg acaggactat    660

aaagatacca ggcgtttccc cctggaagct ccctcgtgcg ctctcctgtt ccgaccctgc    720

cgcttaccgg atacctgtcc gcctttctcc cttcgggaag cgtggcgctt tctcatagct    780

cacgctgtag gtatctcagt tcggtgtaag tcgttcgctc caagctgggc tgtgtgcacg    840

aaccccccgt tcagcccgac cgctgcgcct tatccggtaa ctatcgtctt gagtccaacc    900

cggtaagaca cgacttatcg ccactggcag cagccactgg taacaggatt agcagagcga    960

ggtatgtagg cggtgctaca gagttcttga agtggtggcc taactacggc tacactagaa   1020

gaacagtatt tggtatctgc gctctgctga agccagttac cttcggaaaa agagttggta   1080

gctcttgatc cggcaaacaa accaccgctg gtagcggtgg tttttttgtt tgcaagcagc   1140

agattacgcg cagaaaaaaa ggatctcaag aagatccttt gatcttttct acggggtctg   1200

acgctcagtg gaacgaaaac tcacgttaag ggattttggt catgagatta tcgtcgacaa   1260

ttcgcgcgcg aaggcgaagc ggcatgcatt tacgttgaca ccatcgaatg gtgcaaaacc   1320

tttcgcggta tggcatgata gcgcccggaa gagagtcaat tcagggtggt gaatgtgaaa   1380

ccagtaacgt tatacgatgt cgcagagtat gccggtgtct cttatcagac cgtttcccgc   1440

gtggtgaacc aggccagcca cgtttctgcg aaaacgcggg aaaaagtgga agcggcgatg   1500

gcggagctga attacattcc caaccgcgtg gcacaacaac tggcgggcaa acagtcgttg   1560

ctgattggcg ttgccacctc cagtctggcc ctgcacgcgc cgtcgcaaat tgtcgcggcg   1620

attaaatctc gcgccgatca actgggtgcc agcgtggtgg tgtcgatggt agaacgaagc   1680

ggcgtcgaag cctgtaaagc ggcggtgcac aatcttctcg cgcaacgcgt cagtgggctg   1740

atcattaact atccgctgga tgaccaggat gccattgctg tggaagctgc ctgcactaat   1800

gttccggcgt tatttcttga tgtctctgac cagacaccca tcaacagtat tattttctcc   1860

catgaagacg gtacgcgact gggcgtggag catctggtcg cattgggtca ccagcaaatc   1920

gcgctgttag cgggcccatt aagttctgtc tcggcgcgtc tgcgtctggc tggctggcat   1980

aaatatctca ctcgcaatca aattcagccg atagcggaac gggaaggcga ctggagtgcc   2040

atgtccggtt ttcaacaaac catgcaaatg ctgaatgagg gcatcgttcc cactgcgatg   2100

ctggttgcca acgatcagat ggcgctgggc gcaatgcgcg ccattaccga gtccgggctg   2160
```

-continued cgcgttggtg cggatatctc ggtagtggga tacgacgata ccgaagacag ctcatgttat 2220
atcccgccgt taaccaccat caaacaggat tttcgcctgc tggggcaaac cagcgtggac 2280
cgcttgctgc aactctctca gggccaggcg gtgaagggca atcagctgtt gcccgtctca 2340
ctggtgaaaa gaaaaaccac cctggcgccc aatacgcaaa ccgcctctcc ccgcgcgttg 2400
gccgattcat taatgcagct ggcacgacag gtttcccgac tggaaagcgg gcagtgagcg 2460
caacgcaatt aatgtaagtt agcgcgaatt gtcgaccaaa gcggccatcg tgcctcccca 2520
ctcctgcagt tcgggggcat ggatgcgcgg atagccgctg ctggtttcct ggatgccgac 2580
ggatttgcac tgccggtaga actccgcgag gtcgtccagc ctcaggcagc agctgaacca 2640
actcgcgagg ggatcgagcc cggggtgggc gaagaactcc agcatgagat ccccgcgctg 2700
gaggatcatc cagccggcgt cccggaaaac gattccgaag cccaaccttt catagaaggc 2760
ggcggtggaa tcgaaatctc gtgatggcag gttgggcgtc gcttggtcgg tcatttcgaa 2820
ccccagagtc ccgctcagaa gaactcgtca agaaggcgat agaaggcgat gcgctgcgaa 2880
tcgggagcgg cgataccgta aagcacgagg aagcggtcag cccattcgcc gccaagctct 2940
tcagcaatat cacgggtagc caacgctatg tcctgatagc ggtccgccac acccagccgg 3000
ccacagtcga tgaatccaga aaagcggcca ttttccacca tgatattcgg caagcaggca 3060
tcgccatggg tcacgacgag atcctcgccg tcgggcatgc gcgccttgag cctggcgaac 3120
agttcggctg gcgcgagccc ctgatgctct tcgtccagat catcctgatc gacaagaccg 3180
gcttccatcc gagtacgtgc tcgctcgatg cgatgtttcg cttggtggtc gaatgggcag 3240
gtagccggat caagcgtatg cagccgccgc attgcatcag ccatgatgga tactttctcg 3300
gcaggagcaa ggtgagatga caggagatcc tgccccggca cttcgcccaa tagcagccag 3360
tcccttcccg cttcagtgac aacgtcgagc acagctgcgc aaggaacgcc cgtcgtggcc 3420
agccacgata gccgcgctgc ctcgtcctgc agttcattca gggcaccgga caggtcggtc 3480
ttgacaaaaa gaaccgggcg cccctgcgct gacagccgga acacggcggc atcagagcag 3540
ccgattgtct gttgtgccca gtcatagccg aatagcctct ccacccaagc ggccggagaa 3600
cctgcgtgca atccatcttg ttcaatcatg cgaaacgatc ctcatcctgt ctcttgatca 3660
gatcttgatc ccctgcgcca tcagatcctt ggcggcaaga aagccatcca gtttactttg 3720
cagggcttcc caaccttacc agagggcgcc ccagctggca attccggttc gcttgctgtc 3780
cataaaaccg cccagtctag ctatcgccat gtaagcccac tgcaagctac ctgctttctc 3840
tttgcgcttg cgttttccct tgtccagata gcccagtagc tgacattcat ccggggtcag 3900
caccgtttct gcggactggc tttctacgtg ttccgcttcc tttagcagcc cttgcgccct 3960
gagtgcttgc ggcagcgtg 3979

<210> SEQ ID NO 2
<211> LENGTH: 18
<212> TYPE: DNA
<213> ORGANISM: Artificial sequence
<220> FEATURE:
<223> OTHER INFORMATION: Shine-Dalgarno sequence

<400> SEQUENCE: 2
attataaagg aaaaatta 18

<210> SEQ ID NO 3
<211> LENGTH: 2268
<212> TYPE: DNA

-continued

```
<213> ORGANISM: Artificial sequence
<220> FEATURE:
<223> OTHER INFORMATION: Mature PA sequence including an ETB signal
      sequence
<220> FEATURE:
<221> NAME/KEY: sig_peptide
<222> LOCATION: (1)..(63)
<223> OTHER INFORMATION: ETB signal sequence
<220> FEATURE:
<221> NAME/KEY: CDS
<222> LOCATION: (64)..(2268)
<223> OTHER INFORMATION: Mature PA sequence from B. anthracis

<400> SEQUENCE: 3

atgaataaag taaaatgtta tgttttattt acggcgttac tatcctctct atatgcccat      60

gga gaa gtt aaa cag gaa aac cgt ctg ctc aac gaa tct gag tct tcc       108
    Glu Val Lys Gln Glu Asn Arg Leu Leu Asn Glu Ser Glu Ser Ser
    1               5                   10                  15

tct cag ggc ctg ctg ggt tac tat ttc tct gac ctg aac ttc cag gca       156
Ser Gln Gly Leu Leu Gly Tyr Tyr Phe Ser Asp Leu Asn Phe Gln Ala
                20                  25                  30

ccg atg gtt gta act tct tcc acc acc ggc gac ctg tct att ccg tct       204
Pro Met Val Val Thr Ser Ser Thr Thr Gly Asp Leu Ser Ile Pro Ser
            35                  40                  45

tct gaa ctg gag aac atc ccg tct gaa aac cag tac ttc cag tct gct       252
Ser Glu Leu Glu Asn Ile Pro Ser Glu Asn Gln Tyr Phe Gln Ser Ala
        50                  55                  60

atc tgg tct ggt ttc att aaa gtt aag aaa tct gac gaa tac acc ttc       300
Ile Trp Ser Gly Phe Ile Lys Val Lys Lys Ser Asp Glu Tyr Thr Phe
    65                  70                  75

gct act tct gca gat aac cac gtt act atg tgg gta gac gac cag gaa       348
Ala Thr Ser Ala Asp Asn His Val Thr Met Trp Val Asp Asp Gln Glu
80                  85                  90                  95

gtt atc aac aaa gct tct aac tct aac aaa atc cgt ctg gaa aaa ggc       396
Val Ile Asn Lys Ala Ser Asn Ser Asn Lys Ile Arg Leu Glu Lys Gly
                100                 105                 110

cgt ctg tac cag atc aag att caa tac caa cgt gaa aac ccg acc gag       444
Arg Leu Tyr Gln Ile Lys Ile Gln Tyr Gln Arg Glu Asn Pro Thr Glu
            115                 120                 125

aaa ggt ctg gac ttc aaa ctg tac tgg acc gac tct cag aac aag aaa       492
Lys Gly Leu Asp Phe Lys Leu Tyr Trp Thr Asp Ser Gln Asn Lys Lys
        130                 135                 140

gaa gtt atc tct tcc gac aac ctg cag ctg ccg gaa ctg aaa cag aaa       540
Glu Val Ile Ser Ser Asp Asn Leu Gln Leu Pro Glu Leu Lys Gln Lys
    145                 150                 155

tct tcc aac tct cgt aaa aag cgt tct act tct gct ggt ccg acc gtt       588
Ser Ser Asn Ser Arg Lys Lys Arg Ser Thr Ser Ala Gly Pro Thr Val
160                 165                 170                 175

ccg gac cgt gat aac gac ggt att ccg gac tct ctg gaa gtt gaa ggc       636
Pro Asp Arg Asp Asn Asp Gly Ile Pro Asp Ser Leu Glu Val Glu Gly
                180                 185                 190

tac acc gta gac gtt aaa aac aaa cgt acc ttc ctg tct ccg tgg atc       684
Tyr Thr Val Asp Val Lys Asn Lys Arg Thr Phe Leu Ser Pro Trp Ile
            195                 200                 205

tct aac atc cac gaa aag aaa ggt ctg acc aaa tac aaa tct tcc ccg       732
Ser Asn Ile His Glu Lys Lys Gly Leu Thr Lys Tyr Lys Ser Ser Pro
        210                 215                 220

gag aaa tgg tct acc gct tct gat ccg tac tct gac ttc gaa aaa gtt       780
Glu Lys Trp Ser Thr Ala Ser Asp Pro Tyr Ser Asp Phe Glu Lys Val
    225                 230                 235

act ggt cgt atc gac aaa aac gtt tct ccg gaa gct cgt cac ccg ctg       828
Thr Gly Arg Ile Asp Lys Asn Val Ser Pro Glu Ala Arg His Pro Leu
```

-continued

```
240                 245                 250                 255

gta gca gcg tac ccg atc gtt cac gtt gac atg gaa aac att atc ctg      876
Val Ala Ala Tyr Pro Ile Val His Val Asp Met Glu Asn Ile Ile Leu
                260                 265                 270

tct aaa aac gaa gac cag tct acc cag aac acc gac tct caa act cgt      924
Ser Lys Asn Glu Asp Gln Ser Thr Gln Asn Thr Asp Ser Gln Thr Arg
            275                 280                 285

acc atc tct aaa aac acc tct acc tct cgt act cac acc tct gaa gtt      972
Thr Ile Ser Lys Asn Thr Ser Thr Ser Arg Thr His Thr Ser Glu Val
        290                 295                 300

cac ggt aac gct gag gtt cac gct tct ttc ttt gac atc ggt ggc tct     1020
His Gly Asn Ala Glu Val His Ala Ser Phe Phe Asp Ile Gly Gly Ser
    305                 310                 315

gta tct gct ggt ttc tct aac tct aac tct tct acc gtt gca atc gac     1068
Val Ser Ala Gly Phe Ser Asn Ser Asn Ser Ser Thr Val Ala Ile Asp
320                 325                 330                 335

cac tct ctg tct ctg gct ggt gaa cgt acc tgg gct gaa act atg ggc     1116
His Ser Leu Ser Leu Ala Gly Glu Arg Thr Trp Ala Glu Thr Met Gly
                340                 345                 350

ctg aac acc gca gac acc gct cgt ctg aac gct aac atc cgt tac gtt     1164
Leu Asn Thr Ala Asp Thr Ala Arg Leu Asn Ala Asn Ile Arg Tyr Val
            355                 360                 365

aac acc ggc acc gct ccg atc tac aac gtt ctg ccg act acc tct ctg     1212
Asn Thr Gly Thr Ala Pro Ile Tyr Asn Val Leu Pro Thr Thr Ser Leu
        370                 375                 380

gta ctg ggt aaa aac cag acc ctg gca acc atc aaa gct gac gaa aac     1260
Val Leu Gly Lys Asn Gln Thr Leu Ala Thr Ile Lys Ala Asp Glu Asn
    385                 390                 395

cag ctg tct cag atc ctg gct ccg aac aac tac tat ccg tct aaa aac     1308
Gln Leu Ser Gln Ile Leu Ala Pro Asn Asn Tyr Tyr Pro Ser Lys Asn
400                 405                 410                 415

ctg gct ccg att gca ctg aac gct cag aaa gac ttc tct tcc acc ccg     1356
Leu Ala Pro Ile Ala Leu Asn Ala Gln Lys Asp Phe Ser Ser Thr Pro
                420                 425                 430

atc act atg aac tac aac cag ttc ctg gaa ctg gag aaa acc aaa cag     1404
Ile Thr Met Asn Tyr Asn Gln Phe Leu Glu Leu Glu Lys Thr Lys Gln
            435                 440                 445

ctg cgt ctg gac acc gac cag gtt tac ggt aac atc gct acc tac aac     1452
Leu Arg Leu Asp Thr Asp Gln Val Tyr Gly Asn Ile Ala Thr Tyr Asn
        450                 455                 460

ttc gaa aac ggt cgt gtt cgt gta gac acc ggc tct aac tgg tct gaa     1500
Phe Glu Asn Gly Arg Val Arg Val Asp Thr Gly Ser Asn Trp Ser Glu
    465                 470                 475

gtt ctg ccg cag atc cag gaa acc act gct cgt att atc ttc aac ggt     1548
Val Leu Pro Gln Ile Gln Glu Thr Thr Ala Arg Ile Ile Phe Asn Gly
480                 485                 490                 495

aaa gac ctg aac ctg gtt gaa cgt cgt atc gct gca gta aac ccg tct     1596
Lys Asp Leu Asn Leu Val Glu Arg Arg Ile Ala Ala Val Asn Pro Ser
                500                 505                 510

gac ccg ctg gaa acc act aaa ccg gac atg acc ctg aaa gaa gct ctg     1644
Asp Pro Leu Glu Thr Thr Lys Pro Asp Met Thr Leu Lys Glu Ala Leu
            515                 520                 525

aaa atc gct ttc ggt ttc aac gaa ccg aac ggc aac ctg cag tac cag     1692
Lys Ile Ala Phe Gly Phe Asn Glu Pro Asn Gly Asn Leu Gln Tyr Gln
        530                 535                 540

ggt aaa gat atc acc gaa ttc gac ttt aac ttc gac cag caa acc tct     1740
Gly Lys Asp Ile Thr Glu Phe Asp Phe Asn Phe Asp Gln Gln Thr Ser
    545                 550                 555

cag aac atc aaa aac cag ctg gct gaa ctg aac gct acc aac atc tac     1788
```

-continued

Gln Asn Ile Lys Asn Gln Leu Ala Glu Leu Asn Ala Thr Asn Ile Tyr
560 565 570 575 acc gtt ctg gac aaa atc aag ctg aac gct aaa atg aac att ctg atc 1836
Thr Val Leu Asp Lys Ile Lys Leu Asn Ala Lys Met Asn Ile Leu Ile
580 585 590 cgt gat aaa cgt ttc cac tac gac cgt aac aac atc gct gtt ggt gct 1884
Arg Asp Lys Arg Phe His Tyr Asp Arg Asn Asn Ile Ala Val Gly Ala
595 600 605 gac gaa tct gta gtt aaa gaa gct cac cgt gag gtt atc aac tct tcc 1932
Asp Glu Ser Val Val Lys Glu Ala His Arg Glu Val Ile Asn Ser Ser
610 615 620 acc gaa ggt ctg ctc ctg aac atc gac aaa gat att cgt aaa atc ctg 1980
Thr Glu Gly Leu Leu Leu Asn Ile Asp Lys Asp Ile Arg Lys Ile Leu
625 630 635 tct ggt tac atc gtt gaa atc gaa gac acc gag ggc ctg aaa gaa gtt 2028
Ser Gly Tyr Ile Val Glu Ile Glu Asp Thr Glu Gly Leu Lys Glu Val
640 645 650 655 atc aac gac cgt tac gat atg ctg aac atc tct tcc ctg cgt cag gac 2076
Ile Asn Asp Arg Tyr Asp Met Leu Asn Ile Ser Ser Leu Arg Gln Asp
660 665 670 ggt aaa acc ttc atc gac ttc aaa aag tac aac gat aaa ctg ccg ctg 2124
Gly Lys Thr Phe Ile Asp Phe Lys Lys Tyr Asn Asp Lys Leu Pro Leu
675 680 685 tac atc tct aac ccg aac tac aaa gta aac gtt tac gct gtt acc aaa 2172
Tyr Ile Ser Asn Pro Asn Tyr Lys Val Asn Val Tyr Ala Val Thr Lys
690 695 700 gaa aac acc att atc aac ccg tct gaa aac ggt gac acc tct acc aac 2220
Glu Asn Thr Ile Ile Asn Pro Ser Glu Asn Gly Asp Thr Ser Thr Asn
705 710 715 ggt atc aaa aag atc ctg atc ttc tct aag aaa ggc tac gaa atc ggt 2268
Gly Ile Lys Lys Ile Leu Ile Phe Ser Lys Lys Gly Tyr Glu Ile Gly
720 725 730 735

<210> SEQ ID NO 4
<211> LENGTH: 735
<212> TYPE: PRT
<213> ORGANISM: Artificial sequence
<220> FEATURE:
<223> OTHER INFORMATION: Mature PA sequence including an ETB signal sequence

<400> SEQUENCE: 4

Glu Val Lys Gln Glu Asn Arg Leu Leu Asn Glu Ser Glu Ser Ser Ser
1 5 10 15

Gln Gly Leu Leu Gly Tyr Tyr Phe Ser Asp Leu Asn Phe Gln Ala Pro
20 25 30

Met Val Val Thr Ser Ser Thr Thr Gly Asp Leu Ser Ile Pro Ser Ser
35 40 45

Glu Leu Glu Asn Ile Pro Ser Glu Asn Gln Tyr Phe Gln Ser Ala Ile
50 55 60

Trp Ser Gly Phe Ile Lys Val Lys Lys Ser Asp Glu Tyr Thr Phe Ala
65 70 75 80

Thr Ser Ala Asp Asn His Val Thr Met Trp Val Asp Asp Gln Glu Val
85 90 95

Ile Asn Lys Ala Ser Asn Ser Asn Lys Ile Arg Leu Glu Lys Gly Arg
100 105 110

Leu Tyr Gln Ile Lys Ile Gln Tyr Gln Arg Glu Asn Pro Thr Glu Lys
115 120 125

Gly Leu Asp Phe Lys Leu Tyr Trp Thr Asp Ser Gln Asn Lys Lys Glu

-continued

```
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Gln Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
    370                 375                 380

Leu Gly Lys Asn Gln Thr Leu Ala Thr Ile Lys Ala Asp Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Lys Asp Phe Ser Ser Thr Pro Ile
            420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560
```

-continued

```
Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735


<210> SEQ ID NO 5
<211> LENGTH: 62
<212> TYPE: DNA
<213> ORGANISM: Artificial sequence
<220> FEATURE:
<223> OTHER INFORMATION: M expression control sequence

<400> SEQUENCE: 5

taaaaaactg caaaaaatag tttgacttgt gagcggataa caattaagat gtacccagtt     60

cg                                                                    62


<210> SEQ ID NO 6
<211> LENGTH: 76
<212> TYPE: DNA
<213> ORGANISM: Artificial sequence
<220> FEATURE:
<223> OTHER INFORMATION: M+D expression control sequence

<400> SEQUENCE: 6

taaaaaactg caaaaaatag tttgacttgt gagcggataa caattaagat gtacccagtg     60

tgagcggata acaatt                                                     76


<210> SEQ ID NO 7
<211> LENGTH: 73
<212> TYPE: DNA
<213> ORGANISM: Artificial sequence
<220> FEATURE:
<223> OTHER INFORMATION: U+D expression control sequence

<400> SEQUENCE: 7

ttgtgagcgg ataacaattt gacaccctag ccgataggct ttaagatgta cccagtgtga     60

gcggataaca att                                                        73


<210> SEQ ID NO 8
<211> LENGTH: 122
```

-continued

<212> TYPE: DNA
<213> ORGANISM: Artificial sequence
<220> FEATURE:
<223> OTHER INFORMATION: M+D1 expression control sequence

<400> SEQUENCE: 8
gatccaagct taaaaaactg caaaaaatag tttgacttgt gagcggataa caattaagat 60
gtacccaatt gtgagcggat aacaatttca cacattaaag aggagaaatt acatatggat 120
cg 122

<210> SEQ ID NO 9
<211> LENGTH: 119
<212> TYPE: DNA
<213> ORGANISM: Artificial sequence
<220> FEATURE:
<223> OTHER INFORMATION: M+D2 expression control sequence

<400> SEQUENCE: 9
gatccaagct taaaaaactg caaaaaatag tttgacttgt gagcggataa caattaagat 60
gtacccagtg tgagcggata acaatttcac attaaagagg agaaattaca tatggatcg 119

<210> SEQ ID NO 10
<211> LENGTH: 28
<212> TYPE: DNA
<213> ORGANISM: Artificial sequence
<220> FEATURE:
<223> OTHER INFORMATION: lac operator sequence

<400> SEQUENCE: 10
aattgtgagc ggataacaat ttcacaca 28

<210> SEQ ID NO 11
<211> LENGTH: 16
<212> TYPE: DNA
<213> ORGANISM: Artificial sequence
<220> FEATURE:
<223> OTHER INFORMATION: operator sequence

<400> SEQUENCE: 11
gtgagcggat aacaat 16

<210> SEQ ID NO 12
<211> LENGTH: 4208
<212> TYPE: DNA
<213> ORGANISM: Artificial sequence
<220> FEATURE:
<223> OTHER INFORMATION: pHE4-5 expression plasmid sequence

<400> SEQUENCE: 12
aagcttaaaa aactgcaaaa aatagtttga cttgtgagcg gataacaatt aagatgtacc 60
caattgtgag cggataacaa tttcacacat taaagaggag aaattacata tggaccgttt 120
ccacgctacc tccgctgact gctgcatctc ctacaccccg cgttccatcc cgtgctcgct 180
gctggaatcc tacttcgaaa ccaactccga atgctccaaa ccgggtgtta tcttcctgac 240
caaaaaaggt cgtcgtttct gcgctaaccc gtccgacaaa caggttcagg tttgtatgcg 300
tatgctgaaa ctggacaccc gtatcaaaac ccgtaaaaac tgataaggta cctaagtgag 360
tagggcgtcc gatcgacgga cgcctttttt ttgaattcgt aatcatggtc atagctgttt 420
cctgtgtgaa attgttatcc gctcacaatt ccacacaaca tacgagccgg aagcataaag 480
tgtaaagcct ggggtgccta atgagtgagc taactcacat taattgcgtt gcgctcactg 540

-continued

```
cccgctttcc agtcgggaaa cctgtcgtgc cagctgcatt aatgaatcgg ccaacgcgcg    600
gggagaggcg gtttgcgtat tgggcgctct tccgcttcct cgctcactga ctcgctgcgc    660
tcggtcgttc ggctgcggcg agcggtatca gctcactcaa aggcggtaat acggttatcc    720
acagaatcag gggataacgc aggaaagaac atgtgagcaa aaggccagca aaaggccagg    780
aaccgtaaaa aggccgcgtt gctggcgttt ttccataggc tccgcccccc tgacgagcat    840
cacaaaaatc gacgctcaag tcagaggtgg cgaaacccga caggactata aagataccag    900
gcgtttcccc ctggaagctc cctcgtgcgc tctcctgttc cgaccctgcc gcttaccgga    960
tacctgtccg cctttctccc ttcgggaagc gtggcgcttt ctcatagctc acgctgtagg   1020
tatctcagtt cggtgtaggt cgttcgctcc aagctgggct gtgtgcacga accccccgtt   1080
cagcccgacc gctgcgcctt atccggtaac tatcgtcttg agtccaaccc ggtaagacac   1140
gacttatcgc cactggcagc agccactggt aacaggatta gcagagcgag gtatgtaggc   1200
ggtgctacag agttcttgaa gtggtggcct aactacggct acactagaag aacagtattt   1260
ggtatctgcg ctctgctgaa gccagttacc ttcggaaaaa gagttggtag ctcttgatcc   1320
ggcaaacaaa ccaccgctgg tagcggtggt ttttttgttt gcaagcagca gattacgcgc   1380
agaaaaaaag gatctcaaga agatcctttg atcttttcta cggggtctga cgctcagtgg   1440
aacgaaaact cacgttaagg gattttggtc atgagattat cgtcgacaat tcgcgcgcga   1500
aggcgaagcg gcatgcattt acgttgacac catcgaatgg tgcaaaacct ttcgcggtat   1560
ggcatgatag cgcccggaag agagtcaatt cagggtggtg aatgtgaaac cagtaacgtt   1620
atacgatgtc gcagagtatg ccggtgtctc ttatcagacc gtttcccgcg tggtgaacca   1680
ggccagccac gtttctgcga aaacgcggga aaaagtggaa gcggcgatgg cggagctgaa   1740
ttacattccc aaccgcgtgg cacaacaact ggcgggcaaa cagtcgttgc tgattggcgt   1800
tgccacctcc agtctggccc tgcacgcgcc gtcgcaaatt gtcgcggcga ttaaatctcg   1860
cgccgatcaa ctgggtgcca gcgtggtggt gtcgatggta gaacgaagcg gcgtcgaagc   1920
ctgtaaagcg gcggtgcaca atcttctcgc gcaacgcgtc agtgggctga tcattaacta   1980
tccgctggat gaccaggatg ccattgctgt ggaagctgcc tgcactaatg ttccggcgtt   2040
atttcttgat gtctctgacc agacacccat caacagtatt attttctccc atgaagacgg   2100
tacgcgactg ggcgtggagc atctggtcgc attgggtcac cagcaaatcg cgctgttagc   2160
gggcccatta agttctgtct cggcgcgtct gcgtctggct ggctggcata aatatctcac   2220
tcgcaatcaa attcagccga tagcggaacg ggaaggcgac tggagtgcca tgtccggttt   2280
tcaacaaacc atgcaaatgc tgaatgaggg catcgttccc actgcgatgc tggttgccaa   2340
cgatcagatg gcgctgggcg caatgcgcgc cattaccgag tccgggctgc gcgttggtgc   2400
ggatatctcg gtagtgggat acgacgatac cgaagacagc tcatgttata tcccgccgtt   2460
aaccaccatc aaacaggatt ttcgcctgct ggggcaaacc agcgtggacc gcttgctgca   2520
actctctcag ggccaggcgg tgaagggcaa tcagctgttg cccgtctcac tggtgaaaag   2580
aaaaaccacc ctggcgccca atacgcaaac cgcctctccc cgcgcgttgg ccgattcatt   2640
aatgcagctg gcacgacagg tttcccgact ggaaagcggg cagtgagcgc aacgcaatta   2700
atgtaagtta gcgcgaattg tcgaccaaag cggccatcgt gcctccccac tcctgcagtt   2760
cgggggcatg gatgcgcgga tagccgctgc tggtttcctg gatgccgacg gatttgcact   2820
gccggtagaa ctccgcgagg tcgtccagcc tcaggcagca gctgaaccaa ctcgcgaggg   2880
gatcgagccc ggggtgggcg aagaactcca gcatgagatc cccgcgctgg aggatcatcc   2940
```

-continued agccggcgtc ccggaaaacg attccgaagc ccaacctttc atagaaggcg gcggtggaat 3000
cgaaatctcg tgatggcagg ttgggcgtcg cttggtcggt catttcgaac cccagagtcc 3060
cgctcagaag aactcgtcaa gaaggcgata gaaggcgatg cgctgcgaat cgggagcggc 3120
gataccgtaa agcacgagga agcggtcagc ccattcgccg ccaagctctt cagcaatatc 3180
acgggtagcc aacgctatgt cctgatagcg gtccgccaca cccagccggc cacagtcgat 3240
gaatccagaa aagcggccat tttccaccat gatattcggc aagcaggcat cgccatgggt 3300
cacgacgaga tcctcgccgt cgggcatgcg cgccttgagc ctggcgaaca gttcggctgg 3360
cgcgagcccc tgatgctctt cgtccagatc atcctgatcg acaagaccgg cttccatccg 3420
agtacgtgct cgctcgatgc gatgtttcgc ttggtggtcg aatgggcagg tagccggatc 3480
aagcgtatgc agccgccgca ttgcatcagc catgatggat actttctcgg caggagcaag 3540
gtgagatgac aggagatcct gccccggcac ttcgcccaat agcagccagt cccttcccgc 3600
ttcagtgaca acgtcgagca cagctgcgca aggaacgccc gtcgtggcca gccacgatag 3660
ccgcgctgcc tcgtcctgca gttcattcag ggcaccggac aggtcggtct tgacaaaaag 3720
aaccgggcgc ccctgcgctg acagccggaa cacggcggca tcagagcagc cgattgtctg 3780
ttgtgcccag tcatagccga atagcctctc cacccaagcg gccggagaac ctgcgtgcaa 3840
tccatcttgt tcaatcatgc gaaacgatcc tcatcctgtc tcttgatcag atcttgatcc 3900
cctgcgccat cagatccttg gcggcaagaa agccatccag tttactttgc agggcttccc 3960
aaccttacca gagggcgccc cagctggcaa ttccggttcg cttgctgtcc ataaaaccgc 4020
ccagtctagc tatcgccatg taagcccact gcaagctacc tgctttctct ttgcgcttgc 4080
gttttccctt gtccagatag cccagtagct gacattcatc cggggtcagc accgtttctg 4140
cggactggct ttctacgtgt tccgcttcct ttagcagccc ttgcgccctg agtgcttgcg 4200
gcagcgtg 4208

<210> SEQ ID NO 13
<211> LENGTH: 3984
<212> TYPE: DNA
<213> ORGANISM: Artificial sequence
<220> FEATURE:
<223> OTHER INFORMATION: pHE4-0 expression plasmid sequence

<400> SEQUENCE: 13
aagcttaaaa aactgcaaaa aatagtttga cttgtgagcg gataacaatt aagatgtacc 60
caattgtgag cggataacaa tttcacacat taaagaggag aaattacata tgaaggatcc 120
ttggtaccta agtgagtagg gcgtccgatc gacggacgcc tttttttttga attcgtaatc 180 atggtcatag ctgtttcctg tgtgaaattg ttatccgctc acaattccac acaacatacg 240
agccggaagc ataaagtgta aagcctgggg tgcctaatga gtgagctaac tcacattaat 300
tgcgttgcgc tcactgcccg ctttccagtc gggaaacctg tcgtgccagc tgcattaatg 360
aatcggccaa cgcgcgggga gaggcggttt gcgtattggg cgctcttccg cttcctcgct 420
cactgactcg ctgcgctcgg tcgttcggct gcggcgagcg gtatcagctc actcaaaggc 480
ggtaatacgg ttatccacag aatcagggga taacgcagga aagaacatgt gagcaaaagg 540
ccagcaaaag gccaggaacc gtaaaaaggc cgcgttgctg gcgtttttcc ataggctccg 600
cccccctgac gagcatcaca aaaatcgacg ctcaagtcag aggtggcgaa acccgacagg 660
actataaaga taccaggcgt ttccccctgg aagctccctc gtgcgctctc ctgttccgac 720

-continued

```
cctgccgctt accggatacc tgtccgcctt tctcccttcg ggaagcgtgg cgctttctca    780
tagctcacgc tgtaggtatc tcagttcggt gtaggtcgtt cgctccaagc tgggctgtgt    840
gcacgaaccc cccgttcagc ccgaccgctg cgccttatcc ggtaactatc gtcttgagtc    900
caacccggta agacacgact tatcgccact ggcagcagcc actggtaaca ggattagcag    960
agcgaggtat gtaggcggtg ctacagagtt cttgaagtgg tggcctaact acggctacac   1020
tagaagaaca gtatttggta tctgcgctct gctgaagcca gttaccttcg gaaaaagagt   1080
tggtagctct tgatccggca aacaaaccac cgctggtagc ggtggttttt ttgtttgcaa   1140
gcagcagatt acgcgcagaa aaaaaggatc tcaagaagat cctttgatct tttctacggg   1200
gtctgacgct cagtggaacg aaaactcacg ttaagggatt ttggtcatga gattatcgtc   1260
gacaattcgc gcgcgaaggc gaagcggcat gcatttacgt tgacaccatc gaatggtgca   1320
aaacctttcg cggtatggca tgatagcgcc cggaagagag tcaattcagg gtggtgaatg   1380
tgaaaccagt aacgttatac gatgtcgcag agtatgccgg tgtctcttat cagaccgttt   1440
cccgcgtggt gaaccaggcc agccacgttt ctgcgaaaac gcgggaaaaa gtggaagcgg   1500
cgatggcgga gctgaattac attcccaacc gcgtggcaca acaactggcg ggcaaacagt   1560
cgttgctgat tggcgttgcc acctccagtc tggccctgca cgcgccgtcg caaattgtcg   1620
cggcgattaa atctcgcgcc gatcaactgg gtgccagcgt ggtggtgtcg atggtagaac   1680
gaagcggcgt cgaagcctgt aaagcggcgg tgcacaatct tctcgcgcaa cgcgtcagtg   1740
ggctgatcat taactatccg ctggatgacc aggatgccat tgctgtggaa gctgcctgca   1800
ctaatgttcc ggcgttattt cttgatgtct ctgaccagac acccatcaac agtattattt   1860
tctcccatga agacggtacg cgactgggcg tggagcatct ggtcgcattg ggtcaccagc   1920
aaatcgcgct gttagcgggc ccattaagtt ctgtctcggc gcgtctgcgt ctggctggct   1980
ggcataaata tctcactcgc aatcaaattc agccgatagc ggaacgggaa ggcgactgga   2040
gtgccatgtc cggttttcaa caaaccatgc aaatgctgaa tgagggcatc gttcccactg   2100
cgatgctggt tgccaacgat cagatggcgc tgggcgcaat gcgcgccatt accgagtccg   2160
ggctgcgcgt tggtgcggat atctcggtag tgggatacga cgataccgaa gacagctcat   2220
gttatatccc gccgttaacc accatcaaac aggattttcg cctgctgggg caaaccagcg   2280
tggaccgctt gctgcaactc tctcagggcc aggcggtgaa gggcaatcag ctgttgcccg   2340
tctcactggt gaaaagaaaa accaccctgg cgcccaatac gcaaaccgcc tctccccgcg   2400
cgttggccga ttcattaatg cagctggcac gacaggtttc ccgactggaa agcgggcagt   2460
gagcgcaacg caattaatgt aagttagcgc gaattgtcga ccaaagcggc catcgtgcct   2520
ccccactcct gcagttcggg ggcatggatg cgcggatagc cgctgctggt ttcctggatg   2580
ccgacggatt tgcactgccg gtagaactcc gcgaggtcgt ccagcctcag gcagcagctg   2640
aaccaactcg cgaggggatc gagcccgggg tgggcgaaga actccagcat gagatccccg   2700
cgctggagga tcatccagcc ggcgtcccgg aaaacgattc cgaagcccaa cctttcatag   2760
aaggcggcgg tggaatcgaa atctcgtgat ggcaggttgg gcgtcgcttg gtcggtcatt   2820
tcgaacccca gagtcccgct cagaagaact cgtcaagaag gcgatagaag gcgatgcgct   2880
gcgaatcggg agcggcgata ccgtaaagca cgaggaagcg gtcagcccat tcgccgccaa   2940
gctcttcagc aatatcacgg gtagccaacg ctatgtcctg atagcggtcc gccacaccca   3000
gccggccaca gtcgatgaat ccagaaaagc ggccattttc caccatgata ttcggcaagc   3060
aggcatcgcc atgggtcacg acgagatcct cgccgtcggg catgcgcgcc ttgagcctgg   3120
```

-continued

```
cgaacagttc ggctggcgcg agcccctgat gctcttcgtc cagatcatcc tgatcgacaa   3180
gaccggcttc catccgagta cgtgctcgct cgatgcgatg tttcgcttgg tggtcgaatg   3240
ggcaggtagc cggatcaagc gtatgcagcc gccgcattgc atcagccatg atggatactt   3300
tctcggcagg agcaaggtga gatgacagga gatcctgccc cggcacttcg cccaatagca   3360
gccagtccct tcccgcttca gtgacaacgt cgagcacagc tgcgcaagga acgcccgtcg   3420
tggccagcca cgatagccgc gctgcctcgt cctgcagttc attcagggca ccggacaggt   3480
cggtcttgac aaaaagaacc gggcgcccct gcgctgacag ccggaacacg gcggcatcag   3540
agcagccgat tgtctgttgt gcccagtcat agccgaatag cctctccacc caagcggccg   3600
gagaacctgc gtgcaatcca tcttgttcaa tcatgcgaaa cgatcctcat cctgtctctt   3660
gatcagatct tgatcccctg cgccatcaga tccttggcgg caagaaagcc atccagttta   3720
ctttgcaggg cttcccaacc ttaccagagg gcgccccagc tggcaattcc ggttcgcttg   3780
ctgtccataa aaccgcccag tctagctatc gccatgtaag cccactgcaa gctacctgct   3840
ttctctttgc gcttgcgttt tcccttgtcc agatagccca gtagctgaca ttcatccggg   3900
gtcagcaccg tttctgcgga ctggctttct acgtgttccg cttcctttag cagcccttgc   3960
gccctgagtg cttgcggcag cgtg                                          3984
```

<210> SEQ ID NO 14
<211> LENGTH: 4277
<212> TYPE: DNA
<213> ORGANISM: Artificial sequence
<220> FEATURE:
<223> OTHER INFORMATION: pHE4-a expression plasmid sequence

<400> SEQUENCE: 14

```
aagcttaaaa aactgcaaaa aatagtttga cttgtgagcg gataacaatt aagatgtacc     60
caattgtgag cggataacaa tttcacacat taaagaggag aaattacata tgtgatagat    120
aaaagacgct gaaaccgaat tcttgttgtc caaactgccg ctggaaaacc cggttctgct    180
ggaccgtttc cacgctacct ccgctgactg ctgcatctcc tacaccacgc gttccatccc    240
gtgctcgctg ctggaatcct acttcgaaac caactccgaa tgctccaaac cgggtgttat    300
cttcctgacc aaaaaaggtc gtcgtttctg cgctaacccg tccgacaaac aggttcaggt    360
ttgtatgcgt atgctgaaac tggacacccg tgcggccgct ctagaggatc ctcgaggtac    420
ctaagtgagt agggcgtccg atcgacggac gcctttttt tgaattcgta atcatggtca    480
tagctgtttc ctgtgtgaaa ttgttatccg ctcacaattc cacacaacat acgagccgga    540
agcataaagt gtaaagcctg gggtgcctaa tgagtgagct aactcacatt aattgcgttg    600
cgctcactgc ccgctttcca gtcgggaaac ctgtcgtgcc agctgcatta atgaatcggc    660
caacgcgcgg ggagaggcgg tttgcgtatt gggcgctctt ccgcttcctc gctcactgac    720
tcgctgcgct cggtcgttcg gctgcggcga gcggtatcag ctcactcaaa ggcggtaata    780
cggttatcca cagaatcagg ggataacgca ggaaagaaca tgtgagcaaa aggccagcaa    840
aaggccagga accgtaaaaa ggccgcgttg ctggcgtttt tccataggct ccgcccccct    900
gacgagcatc acaaaaatcg acgctcaagt cagaggtggc gaaacccgac aggactataa    960
agataccagg cgtttccccc tggaagctcc ctcgtgcgct ctcctgttcc gaccctgccg   1020
cttaccggat acctgtccgc ctttctccct tcgggaagcg tggcgctttc tcatagctca   1080
cgctgtaggt atctcagttc ggtgtaggtc gttcgctcca agctgggctg tgtgcacgaa   1140
```

-continued

```
ccccccgttc agcccgaccg ctgcgcctta tccggtaact atcgtcttga gtccaacccg   1200
gtaagacacg acttatcgcc actggcagca gccactggta acaggattag cagagcgagg   1260
tatgtaggcg gtgctacaga gttcttgaag tggtggccta actacggcta cactagaaga   1320
acagtatttg gtatctgcgc tctgctgaag ccagttacct tcggaaaaag agttggtagc   1380
tcttgatccg gcaaacaaac caccgctggt agcggtggtt tttttgtttg caagcagcag   1440
attacgcgca gaaaaaaagg atctcaagaa gatcctttga tcttttctac ggggtctgac   1500
gctcagtgga acgaaaactc acgttaaggg attttggtca tgagattatc gtcgacaatt   1560
cgcgcgcgaa ggcgaagcgg catgcattta cgttgacacc atcgaatggt gcaaaacctt   1620
tcgcggtatg gcatgatagc gcccggaaga gagtcaattc agggtggtga atgtgaaacc   1680
agtaacgtta tacgatgtcg cagagtatgc cggtgtctct tatcagaccg tttcccgcgt   1740
ggtgaaccag gccagccacg tttctgcgaa aacgcgggaa aaagtggaag cggcgatggc   1800
ggagctgaat tacattccca accgcgtggc acaacaactg gcgggcaaac agtcgttgct   1860
gattggcgtt gccacctcca gtctggccct gcacgcgccg tcgcaaattg tcgcggcgat   1920
taaatctcgc gccgatcaac tgggtgccag cgtggtggtg tcgatggtag aacgaagcgg   1980
cgtcgaagcc tgtaaagcgg cggtgcacaa tcttctcgcg caacgcgtca gtgggctgat   2040
cattaactat ccgctggatg accaggatgc cattgctgtg gaagctgcct gcactaatgt   2100
tccggcgtta tttcttgatg tctctgacca gacacccatc aacagtatta ttttctccca   2160
tgaagacggt acgcgactgg gcgtggagca tctggtcgca ttgggtcacc agcaaatcgc   2220
gctgttagcg ggcccattaa gttctgtctc ggcgcgtctg cgtctggctg gctggcataa   2280
atatctcact cgcaatcaaa ttcagccgat agcggaacgg gaaggcgact ggagtgccat   2340
gtccggtttt caacaaacca tgcaaatgct gaatgagggc atcgttccca ctgcgatgct   2400
ggttgccaac gatcagatgg cgctgggcgc aatgcgcgcc attaccgagt ccgggctgcg   2460
cgttggtgcg gatatctcgg tagtgggata cgacgatacc gaagacagct catgttatat   2520
cccgccgtta accaccatca aacaggattt tcgcctgctg gggcaaacca gcgtggaccg   2580
cttgctgcaa ctctctcagg gccaggcggt gaagggcaat cagctgttgc ccgtctcact   2640
ggtgaaaaga aaaaccaccc tggcgcccaa tacgcaaacc gcctctcccc gcgcgttggc   2700
cgattcatta atgcagctgg cacgacaggt ttcccgactg gaaagcgggc agtgagcgca   2760
acgcaattaa tgtaagttag cgcgaattgt cgaccaaagc ggccatcgtg cctccccact   2820
cctgcagttc gggggcatgg atgcgcggat agccgctgct ggtttcctgg atgccgacgg   2880
atttgcactg ccggtagaac tccgcgaggt cgtccagcct caggcagcag ctgaaccaac   2940
tcgcgagggg atcgagcccg gggtgggcga agaactccag catgagatcc ccgcgctgga   3000
ggatcatcca gccggcgtcc cggaaaacga ttccgaagcc caacctttca tagaaggcgg   3060
cggtggaatc gaaatctcgt gatggcaggt tgggcgtcgc ttggtcggtc atttcgaacc   3120
ccagagtccc gctcagaaga actcgtcaag aaggcgatag aaggcgatgc gctgcgaatc   3180
gggagcggcg ataccgtaaa gcacgaggaa gcggtcagcc cattcgccgc caagctcttc   3240
agcaatatca cgggtagcca acgctatgtc ctgatagcgg tccgccacac ccagccggcc   3300
acagtcgatg aatccagaaa agcggccatt ttccaccatg atattcggca agcaggcatc   3360
gccatgggtc acgacgagat cctcgccgtc gggcatgcgc gccttgagcc tggcgaacag   3420
ttcggctggc gcgagcccct gatgctcttc gtccagatca tcctgatcga caagaccggc   3480
ttccatccga gtacgtgctc gctcgatgcg atgtttcgct tggtggtcga atgggcaggt   3540
```

-continued

```
agccggatca agcgtatgca gccgccgcat tgcatcagcc atgatggata ctttctcggc   3600

aggagcaagg tgagatgaca ggagatcctg ccccggcact tcgcccaata gcagccagtc   3660

ccttcccgct tcagtgacaa cgtcgagcac agctgcgcaa ggaacgcccg tcgtggccag   3720

ccacgatagc cgcgctgcct cgtcctgcag ttcattcagg gcaccggaca ggtcggtctt   3780

gacaaaaaga accgggcgcc cctgcgctga cagccggaac acggcggcat cagagcagcc   3840

gattgtctgt tgtgcccagt catagccgaa tagcctctcc acccaagcgg ccggagaacc   3900

tgcgtgcaat ccatcttgtt caatcatgcg aaacgatcct catcctgtct cttgatcaga   3960

tcttgatccc ctgcgccatc agatccttgg cggcaagaaa gccatccagt ttactttgca   4020

gggcttccca accttaccag agggcgcccc agctggcaat tccggttcgc ttgctgtcca   4080

taaaaccgcc cagtctagct atcgccatgt aagcccactg caagctacct gctttctctt   4140

tgcgcttgcg ttttcccttg tccagatagc ccagtagctg acattcatcc ggggtcagca   4200

ccgtttctgc ggactggctt tctacgtgtt ccgcttcctt tagcagccct tgcgccctga   4260

gtgcttgcgg cagcgtg                                                  4277
```

<210> SEQ ID NO 15
<211> LENGTH: 319
<212> TYPE: PRT
<213> ORGANISM: Artificial sequence
<220> FEATURE:
<223> OTHER INFORMATION: LacIq repressor gene sequence

<400> SEQUENCE: 15

```
Met Ala Glu Leu Asn Tyr Ile Pro Asn Arg Val Ala Gln Gln Leu Ala
1               5                   10                  15

Gly Lys Gln Ser Leu Leu Ile Gly Val Ala Thr Ser Ser Leu Ala Leu
            20                  25                  30

His Ala Pro Ser Gln Ile Val Ala Ala Ile Lys Ser Arg Ala Asp Gln
        35                  40                  45

Leu Gly Ala Ser Val Val Val Ser Met Val Glu Arg Ser Gly Val Glu
    50                  55                  60

Ala Cys Lys Ala Ala Val His Asn Leu Leu Ala Gln Arg Val Ser Gly
65                  70                  75                  80

Leu Ile Ile Asn Tyr Pro Leu Asp Asp Gln Asp Ala Ile Ala Val Glu
                85                  90                  95

Ala Ala Cys Thr Asn Val Pro Ala Leu Phe Leu Asp Val Ser Asp Gln
            100                 105                 110

Thr Pro Ile Asn Ser Ile Ile Phe Ser His Glu Asp Gly Thr Arg Leu
        115                 120                 125

Gly Val Glu His Leu Val Ala Leu Gly His Gln Gln Ile Ala Leu Leu
    130                 135                 140

Ala Gly Pro Leu Ser Ser Val Ser Ala Arg Leu Arg Leu Ala Gly Trp
145                 150                 155                 160

His Lys Tyr Leu Thr Arg Asn Gln Ile Gln Pro Ile Ala Glu Arg Glu
                165                 170                 175

Gly Asp Trp Ser Ala Met Ser Gly Phe Gln Gln Thr Met Gln Met Leu
            180                 185                 190

Asn Glu Gly Ile Val Pro Thr Ala Met Leu Val Ala Asn Asp Gln Met
        195                 200                 205

Ala Leu Gly Ala Met Arg Ala Ile Thr Glu Ser Gly Leu Arg Val Gly
    210                 215                 220
```

-continued

```
Ala Asp Ile Ser Val Val Gly Tyr Asp Asp Thr Glu Asp Ser Ser Cys
225                 230                 235                 240

Tyr Ile Pro Pro Leu Thr Thr Ile Lys Gln Asp Phe Arg Leu Leu Gly
                245                 250                 255

Gln Thr Ser Val Asp Arg Leu Leu Gln Leu Ser Gln Gly Gln Ala Val
            260                 265                 270

Lys Gly Asn Gln Leu Leu Pro Val Ser Leu Val Lys Arg Lys Thr Thr
        275                 280                 285

Leu Ala Pro Asn Thr Gln Thr Ala Ser Pro Arg Ala Leu Ala Asp Ser
    290                 295                 300

Leu Met Gln Leu Ala Arg Gln Val Ser Arg Leu Glu Ser Gly Gln
305                 310                 315


<210> SEQ ID NO 16
<211> LENGTH: 264
<212> TYPE: PRT
<213> ORGANISM: Artificial sequence
<220> FEATURE:
<223> OTHER INFORMATION: Kanamycin resistance gene sequence

<400> SEQUENCE: 16

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

-continued

```
<210> SEQ ID NO 17
<211> LENGTH: 18
<212> TYPE: DNA
<213> ORGANISM: Artificial sequence
<220> FEATURE:
<223> OTHER INFORMATION: pHE4 Shine-Dalgarno sequence

<400> SEQUENCE: 17

attaaagagg agaaatta                                              18


<210> SEQ ID NO 18
<211> LENGTH: 12
<212> TYPE: DNA
<213> ORGANISM: Artificial sequence
<220> FEATURE:
<223> OTHER INFORMATION: Shine Dalgarno sequence based on phoA promoter

<400> SEQUENCE: 18

gtaaaggaag ta                                                    12
```

MODIFIED SHINE-DALGARNO SEQUENCES AND METHODS OF USE THEREOF

CROSS-REFERENCE TO RELATED APPLICATIONS

This application is a continuation of International Application Ser. No. PCT/US03/19786, filed Jun. 25, 2003, which claims benefit under 35 U.S.C. 119(e) to U.S. Provisional Application Ser. No. 60/391,433, filed Jun. 26, 2002, and 60/406,630, filed Aug. 29, 2002, each of which is hereby incorporated by reference in its entirety.

FIELD OF THE INVENTION

The present invention relates to novel Shine-Dalgarno (ribosome binding site) sequences, vectors containing such sequences, and host cells transformed with these vectors. The present invention also relates to methods of use of such sequences, vectors, and host cells for the efficient production of proteins and fragments thereof in prokaryotic systems, and in one aspect of the invention, provides for high efficiency production of soluble protein in prokaryotic systems.

BACKGROUND OF THE INVENTION

The level of production of a protein in a host cell is determined by three major factors: the number of copies of its structural gene within the cell, the efficiency with which the structural gene copies are transcribed and the efficiency with which the resulting messenger RNA ("mRNA") is translated. The transcription and translation efficiencies are, in turn, dependent on nucleotide sequences that are normally situated ahead of the desired structural genes or the translated sequence. These nucleotide sequences, also known as expression control sequences, define, inter alia, the locations at which RNA polymerase binds (the promoter sequence to initiate transcription; see also EMBO J. 5:2995–3000 (1986)) and at which ribosomes bind and interact with the mRNA (the product of transcription) to initiate translation.

In most prokaryotes, the purine-rich ribosome binding site known as the Shine-Dalgarno (S-D) sequence assists with the binding and positioning of the 30S ribosome component relative to the start codon on the mRNA through interaction with a pyrimidine-rich region of the 16S ribosomal RNA. See, e.g., Shine & Dalgarno, Proc. Natl. Acad. Sci. USA 71:1342–46 (1976). The S-D sequence is located on the mRNA downstream from the start of transcription and upstream from the start of translation, typically from 4–14 nucleotides upstream of the start codon, and more typically from 8–10 nucleotides upstream of the start codon. Because of the role of the S-D sequence in translation, there is a direct relationship between the efficiency of translation and the efficiency (or strength) of the S-D sequence.

Not all S-D sequences have the same efficiency, however. Accordingly, prior attempts have been made to increase the efficiency of ribosomal binding, positioning, and translation by, inter alia, changing the distance between the S-D sequence and the start codon, changing the composition of the space between the S-D sequence and the start codon, modifying an existing S-D sequence, using a heterologous S-D sequence, and manipulating of the secondary structure of mRNA during the initiation of translation. Despite these changes, however, success in increasing of protein expression efficiency in prokaryotic systems has remained an elusive and unpredictable goal due to a variety of factors, including, inter alia, the host cells used, the expression control sequences (including the S-D sequence) used, and the characteristics of the gene and protein being expressed. See, e.g., Stenstrom, et al., Gene 273(2):259–265 (2001); Komarova, et al., Bioorg. Kbim. 27(4)282–290 (2001); Stenstrom, et al., Gene 263(1–2):273–284 (2001); and Mironova, et al., Microbiol. Res. 154(1):35–41 (1999). For example, efficient expression of soluble *B. anthracis* protective antigen (PA) has proved difficult in *E. coli*. See, e.g., Sharma, et al. Protein Expression and Purification 7:33–38 (1996) (indicating 0.5 mg/L at 70% purity); Chauhan, et al. Biochem. Biophys. Res. Commun.; 283(2):308–15 (2001) (indicating 125 mg/L); Gupta, et al. Protein Expr. Purif. 16(3):369–76 (1999) (indicating 2 mg/L).

Accordingly, there remains a demand in the art for compositions and methods for increasing the efficiency of ribosome binding and translation in prokaryotic systems, thereby resulting in increased efficiency of protein expression. This demand is especially strong for proteins that are difficult to express in existing systems, and for proteins that are desired in large quantity for pharmacological, therapeutic, or industrial use.

SUMMARY OF THE INVENTION

The present invention encompasses novel Shine-Dalgarno sequences that result in increased efficiency of protein expression in prokaryotic systems. The present invention further relates to vectors comprising such S-D sequences and host cells transformed with such vectors. In particular embodiments, the present invention relates to methods for producing proteins and fragments thereof in prokaryotic systems using such S-D sequences, vectors, and host cells. In certain embodiments, methods of use of the S-D sequences, vectors, and host cells of the invention provide high efficiency production of soluble protein in prokaryotic systems, including prokaryotic in vitro translation systems.

In particular embodiments of the invention, the novel S-D sequence comprises (or alternately consists of) SEQ ID NO:2. In additional embodiments, the novel S-D sequence comprises (or alternately consists of) nucleotides 4–13 of SEQ ID NO:2. The invention also encompasses the S-D sequence of SEQ ID NO:18, described at paragraph 0426 of U.S. Provisional Application No. 60/368,548, filed Apr. 1, 2002, and in U.S. Provisional Application No. 60/331,478, filed Nov. 16, 2001, each of which is hereby incorporated by reference herein in its entirety.

The protein or fragment thereof may be of prokaryotic, eukaryotic, or viral origin, or may be artificial. In particular embodiments, the S-D sequences, vectors, and host cells of the invention are used to express *B. anthracis* protective antigen (PA), mutated protective antigens (mPAs) (See, e.g., Sellman et al, JBC 276(11):8371–8376 (2001)), TL3, TL6, or other proteins. In certain embodiments, the S-D sequences, vectors, and host cells of the invention are used to express proteins that have previously been difficult to express in prokaryotic systems. The present invention also encompasses the combination of novel S-D sequences with a variety of expression control sequences, such as those described in detail in U.S. Pat. No. 6,194,168 (which is hereby incorporated by reference herein in its entirety), and in particular, expression control sequences comprising at least a portion of one or more lac operator sequences and a phage promoter comprising a −30 region.

BRIEF DESCRIPTION OF THE DRAWINGS

FIG. 1 depicts a Shine-Dalgarno sequence of the present invention (SEQ ID NO: 2) and the Shine-Dalgarno sequence contained in the pHE4 expression vector (SEQ ID NO:17) (See U.S. Pat. No. 6,194,168). Bases matching the S-D sequence of the present invention (SEQ ID NO:2) are highlighted.

DETAILED DESCRIPTION OF THE INVENTION

Figure 2A:
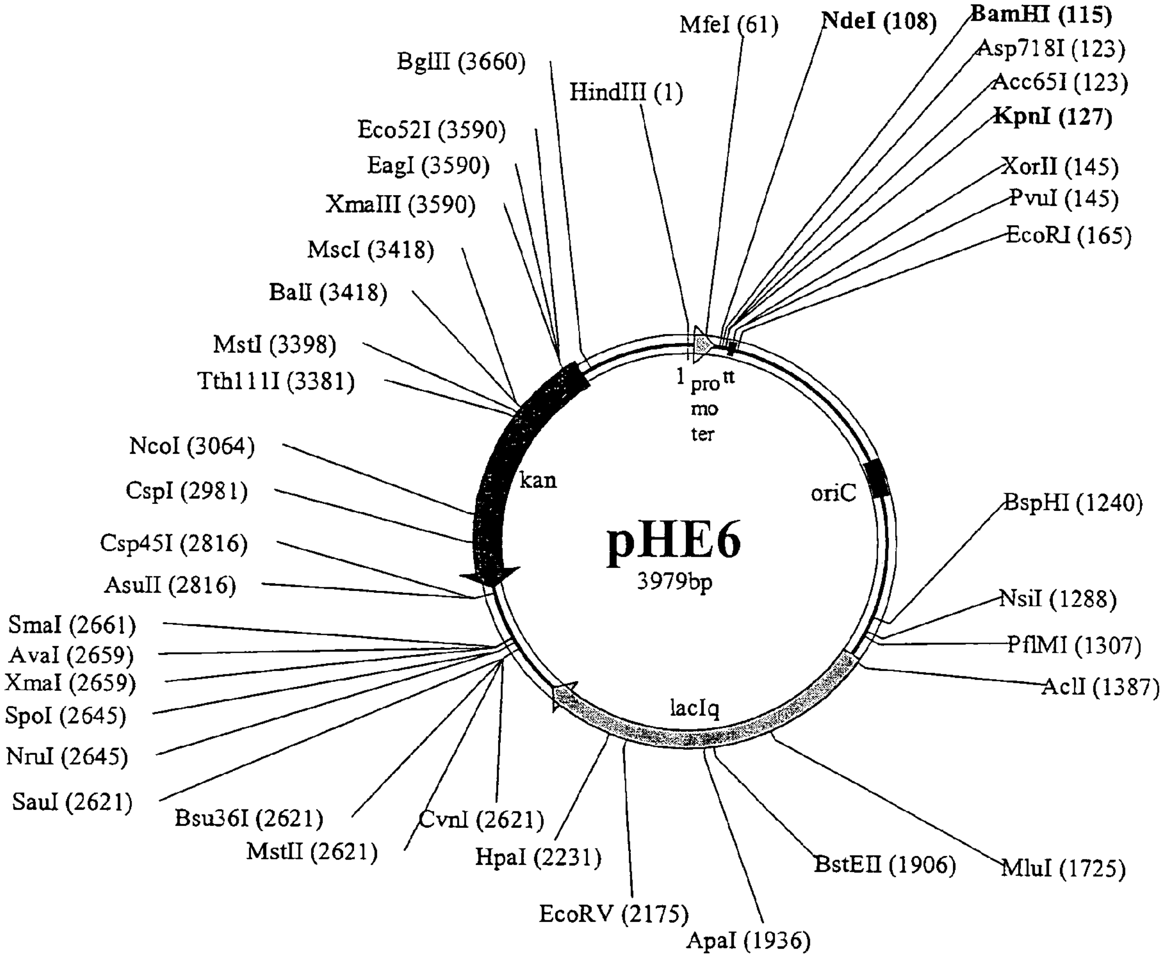
FIG. 2A depicts a map of the pHE6 vector (SEQ ID NO:1), which incorporates a S-D sequence of the invention.
Figure 2B:
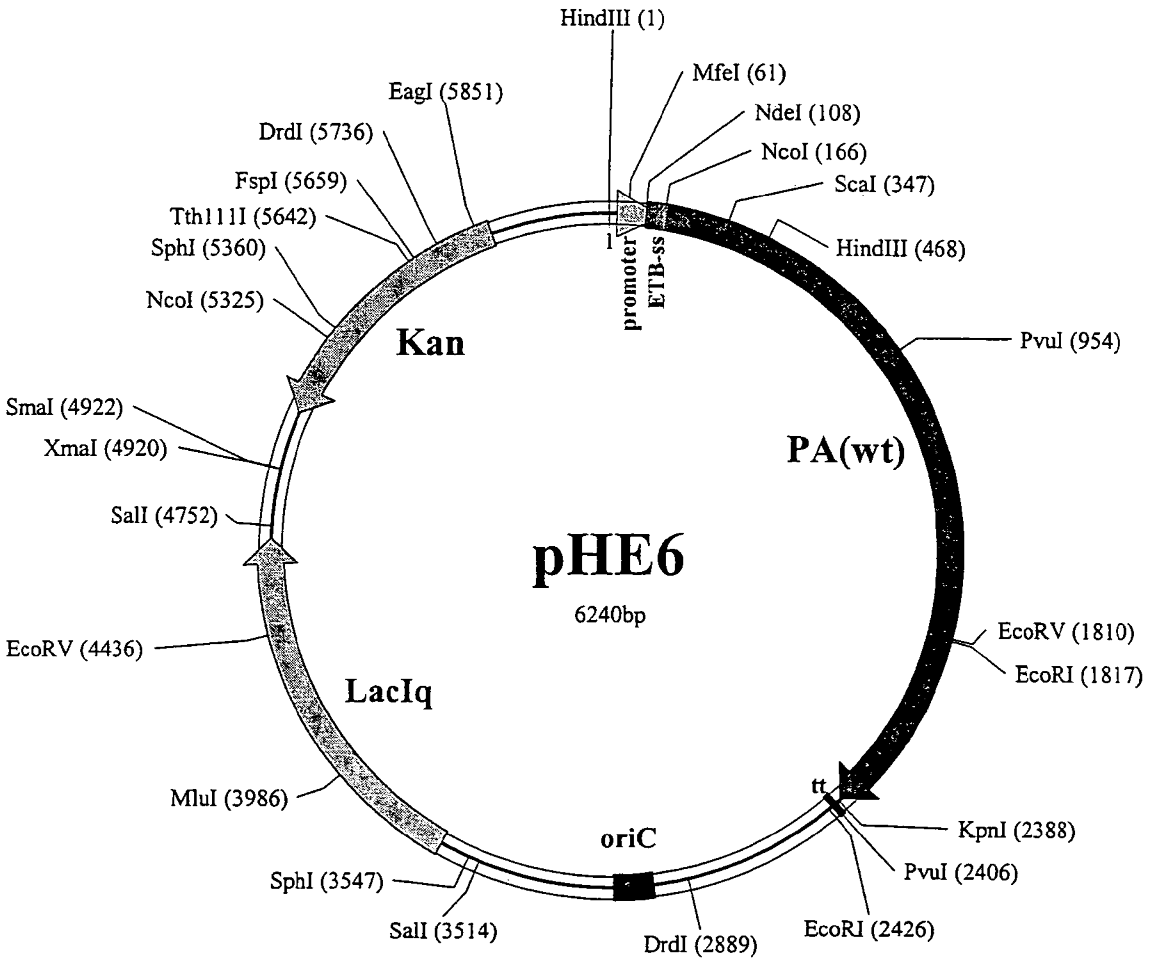
FIG. 2B depicts the pHE6 vector (SEQ ID NO:1) with the gene encoding mature *Bacillus anthracis* PA including an ETB signal sequence (SEQ ID NO:3) inserted.
Figure 3A:
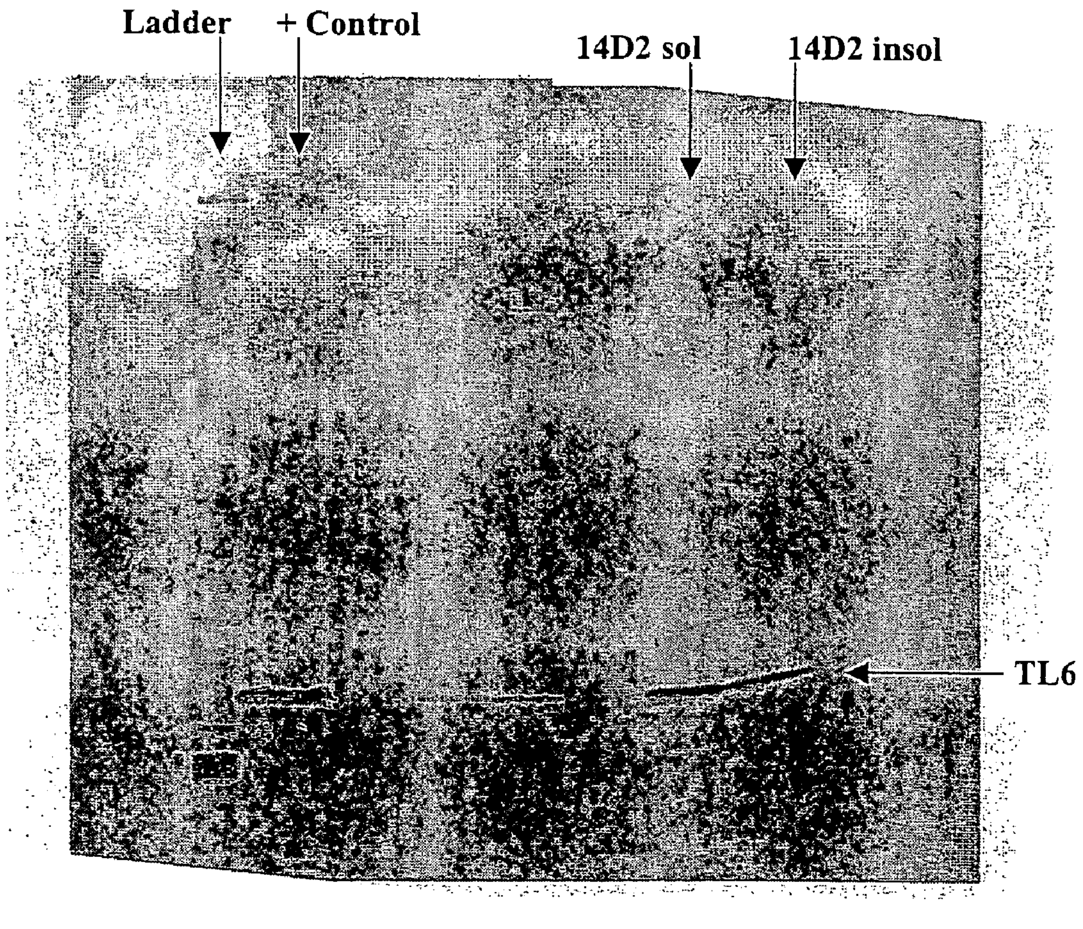
FIGS. 3A–3B compare the efficiency of TL6 protein expression using the pHE4 vector (FIG. 3B) versus the pHE6 vector (FIG. 3A), which uses a S-D sequence of the invention. In particular, increased soluble TL6 expression with the pHE6 vector can be seen in FIG. 3A as a lack of "shadow" in the gel.
Figure 3B:
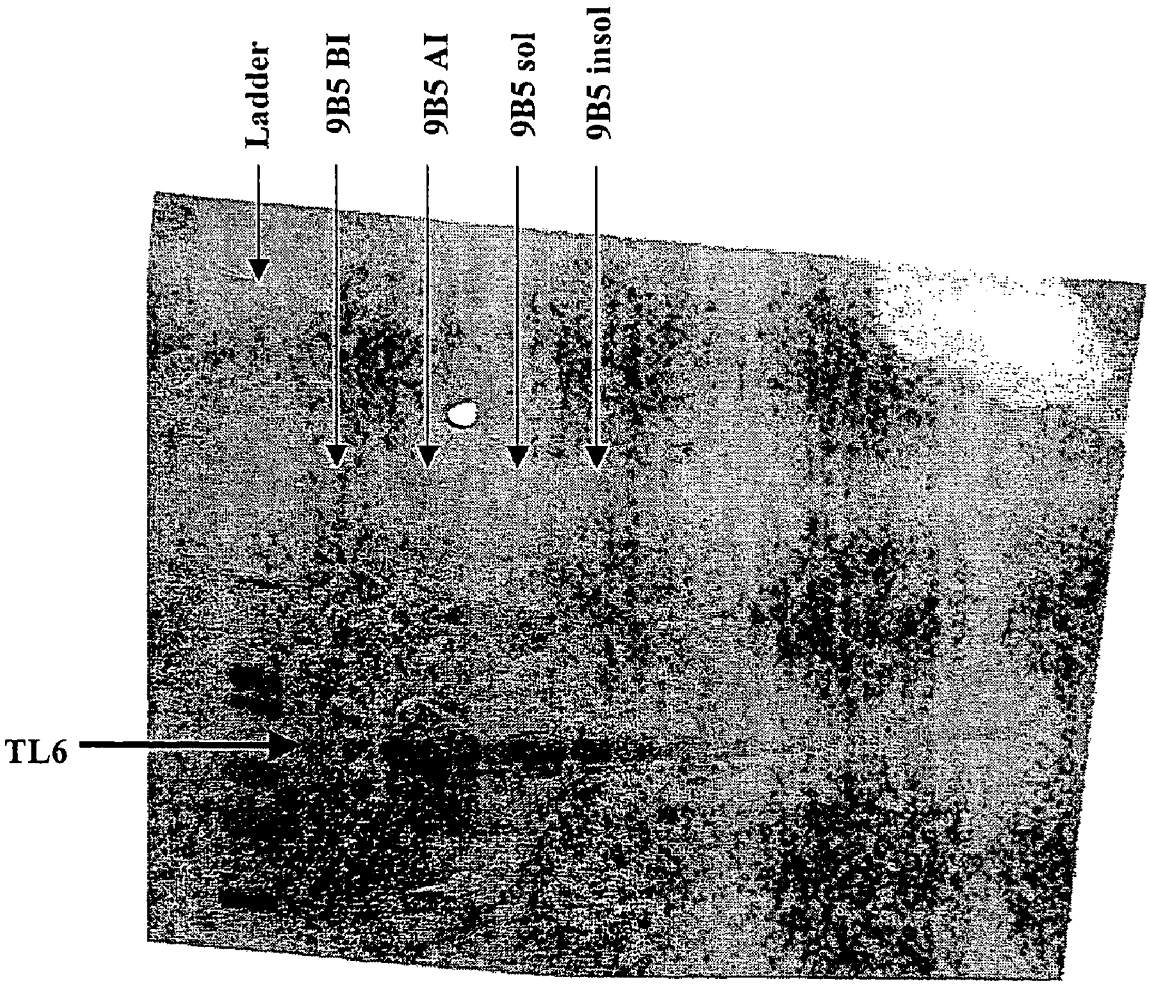

The instant invention is directed to novel Shine-Dalgarno (ribosomal binding site) sequences. These S-D sequences result in increased efficiency of protein expression in prokaryotic systems. The S-D sequences of the present invention have been optimized through modification of several nucleotides. See, e.g., FIG. 1. In particular embodiments, the S-D sequences of the present invention comprise (or alternately consist of) SEQ ID NO:2. In additional embodiments, the S-D sequences of the present invention comprise (or alternately consist of) nucleotides 4–13 of SEQ ID NO:2. In other embodiments, the S-D sequences of the present invention comprise (or alternately consist of) SEQ ID NO:18.

In many embodiments, the S-D sequences of the present invention are used in prokaryotic cells. Exemplary bacterial cells suitable for use with the instant invention include *E. coli, B. subtilis, S. aureus, S. typhimurium*, and other bacteria used in the art. In other embodiments, the S-D sequences of the present invention are used in prokaryotic in vitro transcription systems.

The present invention also relates to vectors and plasmids comprising one or more S-D sequences of the invention. Such vectors and plasmids generally also further comprise one or more restriction enzyme sites downstream of the S-D sequence for cloning and expression of a gene or polynucleotide of interest.

In certain embodiments, vectors and plasmids of the present invention further comprise additional expression control sequences, including but not limited to those described in U.S. Pat. No. 6,194,168, and in particular, M (SEQ ID NO:5), M+D (SEQ ID NO:6), U+D (SEQ ID NO:7), M+D1 (SEQ ID NO:8), and M+D2 (SEQ ID NO:9). More generally, the expression control sequence elements contemplated include bacterial or phage promoter sequences and functional variants thereof, whether natural or artificial; operator/repressor systems; and the lacIq gene (which confers tight regulation of the lac operator by blocking transcription of down-stream (i.e., 3') sequences).

The lac operator sequences contemplated for use in vectors and plasmids of the instant invention comprise (or alternately consist of) the entire lac operator sequence represented by the sequence 5' AATTGTGAGCGGATAACAATTTCACACA 3' (SEQ ID NO:10), or a portion thereof that retains at least partial activity, as described in U.S. Pat. No. 6,194,168. Activity is routinely determined using techniques well known in the art to measure the relative repressability of a promoter sequence in the absence of an inducer, such as IPTG. This is done by comparing the relative amounts of protein expressed from expression control sequences comprising portions of the lac operator sequence and full-length lac operator sequence. The partial operator sequence is measured relative to the full-length lac operator sequence (e.g., SEQ ID NO:10). In one embodiment, partial activity for the purposes of the present invention means activity reduced by no more than 100 fold relative to the full-length sequence. In alternative embodiments, partial activity for the purpose of the present invention means activity reduced by no more than 75, 50, 25, 20, 15, and 10 fold, relative to the full-length lac operator sequence. In a preferred embodiment, the activity of a partial operator sequence is reduced by no more than 10 fold relative to the activity of the full-length sequence.

In many embodiments, one or more S-D sequences of the invention are used in a vector comprising a T5 phage promoter sequence and two lac operator sequences wherein at least a portion of the full-length lac operator sequence (SEQ ID NO:10) is located within the spacer region between −12 and −30 of the expression control sequences described in U.S. Pat. No. 6,194,168. In particular embodiments, the operator sequence comprises (or alternately consists of) at least the sequence 5'-GTGAGCGGATAACAAT-3' (SEQ ID NO:11).

The previously mentioned lac-operator sequences are negatively regulated by the lac-repressor. The corresponding repressor gene can be introduced into the host cell in a vector or through integration into the chromosome of a bacterium by known methods, such as by integration of the lacIq gene. See, e.g., Miller et al, supra; Calos, (1978) Nature 274: 762–765. The vector encoding the repressor molecule may be the same vector that contains the expression control sequences and a gene or polynucleotide of interest or may be a separate vector.

The S-D sequences of the invention can routinely be inserted using procedures known in the art into any suitable expression vector that can replicate in gram-negative and/or gram-positive bacteria. See, e.g., Sambrook et al., Molecular Cloning: A Laboratory Manual (Cold Spring Harbor, N.Y. 2nd ed. 1989); Ausubel et al., Current Protocols in Molecular Biology (Green Pub. Assoc. and Wiley Intersciences, N.Y.). Suitable vectors and plasmids can be constructed from segments of chromosomal, non-chromosomal and synthetic DNA sequences, such as various known plasmid and phage DNAs. See, e.g., Sambrook et al., Molecular Cloning: A Laboratory Manual (Cold Spring Harbor, N.Y. 2nd ed. 1989). Especially suitable vectors include plasmids of the pDS family. See Bujard et al, (1987) Methods in Enzymology, 155:416–4333. Additional examples of preferred suitable plasmids include pBR322 and pBluescript (Stratagene, La Jolla, Calif.) based plasmids. Still additional examples of preferred suitable plasmids include pUC-based vectors, including pUC18 and pUC19 (New England Biolabs, Beverly, Mass.) and pREP4 (Qiagen Inc., Chatsworth, Calif.). Portions of vectors and plasmids encoding desired functions may also be combined to form new vectors with desired characteristics. For example, the origin of replication of pUC19 may be recombined with the kanamycin resistance gene of pREP4 to create a new vector with both desired characteristics.

Preferably, vectors and plasmids comprising one or more S-D sequences of the invention also contain sequences that allow replication of the plasmid to high copy number in the host bacterium of choice. Additionally, vector or plasmid embodiments of the invention that comprise expression control sequences may further comprise a multiple cloning site immediately downstream of the expression control sequences and the S-D sequence.

Vectors and plasmids comprising one or more S-D sequences of the invention may further comprise genes conferring antibiotic resistance. Preferred genes are those conferring resistance to ampicillin, chloramphenicol, and tetracycline. Especially preferred genes are those conferring resistance to kanamycin.

The optimized S-D ribosomal binding site of the invention can also be inserted into the chromosome of gram-negative and gram-positive bacterial cells using techniques known in the art. In this case, selection agents such as antibiotics, which are generally required when working with vectors, can be dispensed with.

Proteins of interest that can be expressed using the S-D sequences, vectors, and host cells of the invention include prokaryotic, eukaryotic, viral, or artificial proteins. Such proteins include, but are not limited to: enzymes; hormones; proteins having immunoregulatory, antiviral or antitumor activity; antibodies and fragments thereof (e.g., Fab, F(ab), $F(ab)_2$, single-chain Fv, disulfide-linked Fv); or antigens. In preferred embodiments, the protein to be expressed is *B. anthracis* protective antigen (PA), mutated protective antigens (mPAs) (See, e.g., Sellman et al, JBC 276(11):8371–8376 (2001)), TL3, or TL6. Any effective signal sequence may be used in combination with the gene or polynucleotide of interest. In a preferred embodiment, the ETB signal sequence is used to enhance the expression of soluble protein.

The S-D sequences of the present invention provide for increased efficiency of protein expression in prokaryotic systems. Efficient expression means that the level of protein expression to be expected when using the S-D sequences of the instant invention is generally higher than levels previously reported in the art. In preferred embodiments, the resultant expressed protein can be highly purified to levels greater than 90% purity by RF-HPLC. Particularly preferred purity levels include 90, 91, 92, 93, 94, 95, 96, 97, 98, 99, and near 100% purity, all of which are encompassed by the instant invention. It is expressly contemplated by the invention that the addition of one or more S-D sequences of the invention into any prokaryotic-based expression system, including and in addition to *E. coli* expression systems, will result in increased and more efficient protein expression.

The present invention also relates to methods of using the S-D sequences, vectors, plasmids, and host cells of the invention to produce proteins and fragments thereof. In one embodiment of the invention, a desired protein is produced by a method comprising:

(a)transforming a bacterium with a vector in which a polynucleotide encoding a desired protein is operably linked to a S-D sequence of the invention;

(b)culturing the transformed bacterium under suitable growth conditions; and (c) isolating the desired protein from the culture.

In another embodiment of the invention, a desired protein is produced by a method comprising:

(a)inserting a S-D sequence of the invention and an expression control sequence into the chromosome of a suitable bacterium, wherein the S-D sequence and expression control sequence are each operably linked to a polynucleotide encoding a desired protein;

(b)cultivating the bacterium under suitable growth conditions; and (c) isolating the desired protein from the culture.

The selection of a suitable host organism is determined by various factors that are well known in the art. Factors to be considered include, for example, compatibility with the selected vector, toxicity of the expression product, expression characteristics, necessary biological safety precautions and costs.

Suitable host organisms include, but are not limited to, gram-negative and gram-positive bacteria, such as *E. coli, B. subtilis, S. aureus*, and *S. typhimurium* strains. Preferred *E. coli* strains include DH5α (Gibco-BRL, Gaithersburg, Md.), XL-1 Blue (Stratagene), and W3110 (ATCC No. 27325). Other *E. coli* strains that can be used according to the present invention include other generally available strains such as *E. coli* 294 (ATCC No. 31446), *E. coli* RR1 (ATCC No. 31343) and M15.

EXAMPLES

The examples which follow are set forth to aid in understanding the invention but are not intended to, and should not be construed to, limit the scope of the invention in any way. The examples do not include detailed descriptions for conventional methods employed in the art, such as for the construction of vectors, the insertion of genes encoding polypeptides of interest into such vectors, or the introduction of the resulting plasmids into bacterial hosts. Such methods are described in numerous publications and can be carried out using recombinant DNA technology methods which are well known in the art. See, e.g., Sambrook et al., Molecular Cloning: A Laboratory Manual (Cold Spring Harbor, N.Y. 2nd ed. 1989); Ausubel et al., Current Protocols in Molecular Biology (Green Pub. Assoc. and Wiley Intersciences, N.Y.).

Example 1 pHE6 Design

The S-D sequence used in pHE6 (SEQ ID NO:2) was based on the S-D sequence of the pHE4 expression vector (SEQ ID NO:17) (See U.S. Pat. No. 6,194,168), with three base pair changes made as indicated in FIG. 1. Additionally, the pHE6 plasmid encodes the aminoglycoside phosphotransferase protein (conferring kanamycin resistance), the lacIq repressor, and includes a Co1E1 replicon. Construction of the pHE4 plasmid upon which the pHE6 plasmid is based is described in U.S. Pat. No. 6,194,168.

Example 2

Method of Making and Purifying PA in *Escherichia coli* K-12

Figure 4:
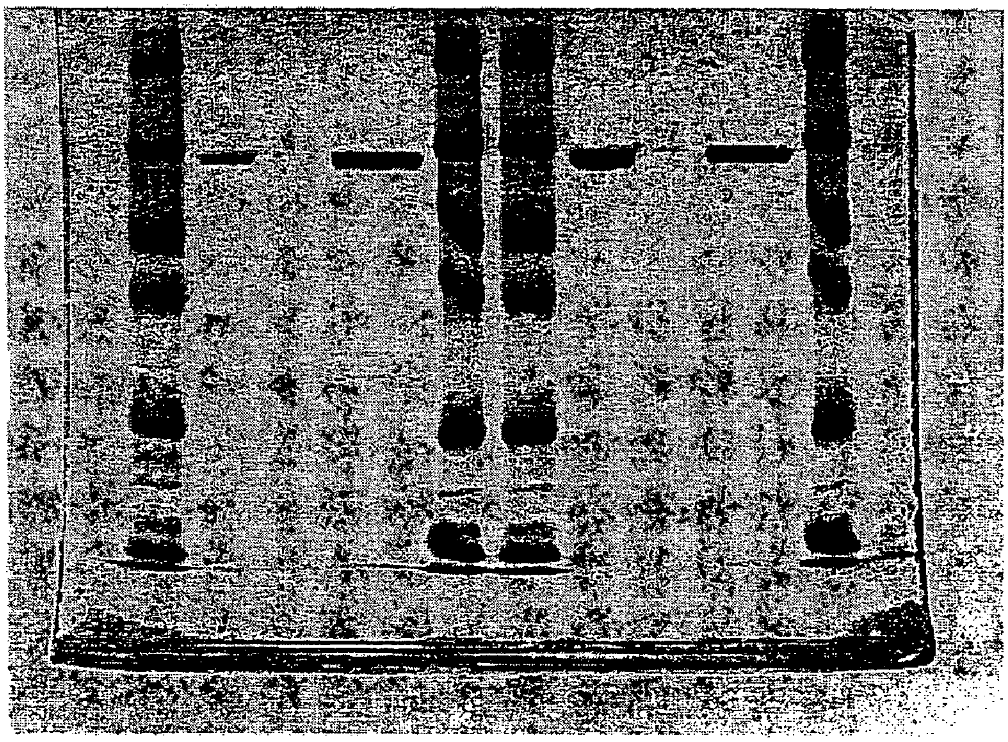
FIG. 4 depicts a gel showing the quantity and quality of PA after expression using pHE6 and subsequent purification. Using the compositions and methods of the invention, approximately 150 mg/L of soluble PA at greater than 96% purity (as measured by RP-HPLC) was obtained.

Using the following method, a post-purification final yield of soluble PA greater than 2 g from 1 kg of *E. coli* cell paste (approximately 150 mg/L) can be obtained from either shake flasks or bioreactors. See FIG. 4. The purity of such soluble PA, as judged by RP-HPLC analysis, is greater than 96–98%.

The bacterial host strain used for the production of recombinant wild-type PA from a recombinant plasmid DNA molecule is an *E. coli* K-12 derived strain. To express protein from the expression vectors, *E. coli* cells were transformed with the expression vectors and grown overnight (O/N) at 30° C. in 4L shaker flasks containing 1L Luria broth medium supplemented with kanamycin. The cultures were started at optical density 600 $\lambda$ (O.D.$^{600}$) of 0.1. IPTG was added to a final concentration of 1 mM when the culture reached an O.D.$^{600}$ of between 0.4 and 0.6. IPTG induced cultures were grown for an additional 3 hours. Cells were then harvested using methods known in the art, and the level of protein was detected using Western blot analysis. Soluble PA was then extracted from the periplasm and clarified by conventional means. The clarified supernatant was then purified using a Q Sepharose HP column (Amersham), concentrated, and further purified using a Biogel Hydroxyapatite HP column (BioRAD). Using the expression control sequence M+D1 (SEQ ID NO:8), high levels of repression in the absence of IPTG, and high levels of induced expression in the presence of IPTG were obtained.

Deposit of Microorganisms

Plasmid pHE6 was deposited with the American Type Culture Collection,

University Boulevard, Manassas, Va. 20110–2209 on Jun. 20, 2002 and was given Accession No. PTA-4474. This culture has been accepted for deposit under the provisions of the Budapest Treaty on the International Recognition of Microorganisms for the Purposes of Patent Proceedings.

The disclosures of all publications (including patents, patent applications, journal articles, laboratory manuals, books, or other documents) cited herein are hereby incorporated by reference in their entireties.

The present invention is not to be limited in scope by the specific embodiments described herein, which are intended as illustrations of individual aspects of the invention. Functionally equivalent methods and components are within the scope of the invention, in addition to those shown and described herein and will become apparent to those skilled in the art from the foregoing description and accompanying drawings. Such modifications are intended to fall within the scope of the appended claims.

What is claimed is:

1. An isolated polynucleotide comprising a Shine-Dalgarno sequence selected from the group consisting of:

(a) SEQ ID NO:2;

(b) polynucleotides 4–13 of SEQ ID NO:2; and (c) SEQ ID NO:18;

wherein said Shine-Dalgarno sequence is between 4–14 nucleotides upstream from a start codon.

2. The isolated polynucleotide of claim 1 wherein the Shine-Dalgarno sequence is (a).

3. The isolated polynucleotide of claim 1 wherein the Shine-Dalgarno sequence is (b).

4. The isolated polynucleotide of claim 1 wherein the Shine-Dalgarno Dalgarno sequence is (c).

5. A vector comprising a Shine-Dalgarno sequence selected from a group consisting of:

(a) SEQ ID NO:2;

(b) polynucleotides 4–13 of SEQ ID NO:2; and (c) SEQ ID NO:18;

wherein said Shine-Dalgarno sequence is between 4–14 nucleotides upstream from a start codon.

6. The vector of claim 5 wherein the Shine-Dalgarno sequence is (a).

7. The vector of claim 5 wherein the Shine-Dalgarno sequence is (b).

8. The vector of claim 5 wherein the Shine-Dalgarno sequence is (c).

9. The vector of claim 5 wherein said Shine-Dalgarno sequence is operably associated with a polynucleotide encoding a protein or fragment thereof.

10. The vector of claim 9, wherein said polynucleotide encodes SEQ ID NO:4.

11. The vector of claim 9, wherein said polynucleotide is operably associated with an expression control sequence.

12. A method of producing a vector comprising inserting the Shine-Dalgarno sequence of claim 1 into a vector.

13. A method of producing a host cell comprising transducing, transforming or transfecting a host cell with the vector of claim 5.

14. A recombinant host cell comprising the Shine-Dalgarno sequence of claim 1.

15. A recombinant host cell comprising the vector of claim 5.

16. A recombinant host cell comprising the vector of claim 9.

17. A method of producing protein, comprising:

(a) culturing the host cell of claim 16 under conditions suitable to produce the protein or fragment thereof; and (b) recovering the protein or fragment thereof from the cell culture.

18. The method of claim 17, wherein said polynucleotide encodes SEQ ID NO:4.

19. The isolated polynucleotide sequence of claim 1, wherein said Shine-Dalgarno Dalgarno sequence is between 8–10 nucleotides upstream from a start codon.

20. The vector of claim 5, wherein said Shine-Dalgarno sequence is between 8–10 nucleotides upstream from a start codon.

* * * * *